US009495771B2

United States Patent
El Fakhri et al.

(10) Patent No.: US 9,495,771 B2
(45) Date of Patent: Nov. 15, 2016

(54) SYSTEMS AND METHODS FOR MOTION CORRECTION IN POSITRON EMISSION TOMOGRAPHY IMAGING

(71) Applicants: Georges El Fakhri, Brookline, MA (US); Chuan Huang, Boston, MA (US); Jinsong Ouyang, Lexington, MA (US); Quanzheng Li, Cambridge, MA (US); Yoann Petibon, Cambridge, MA (US); Joyita Dutta, Brookline, MA (US)

(72) Inventors: Georges El Fakhri, Brookline, MA (US); Chuan Huang, Boston, MA (US); Jinsong Ouyang, Lexington, MA (US); Quanzheng Li, Cambridge, MA (US); Yoann Petibon, Cambridge, MA (US); Joyita Dutta, Brookline, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 14/274,340

(22) Filed: May 9, 2014

(65) Prior Publication Data

US 2014/0334702 A1 Nov. 13, 2014

Related U.S. Application Data

(60) Provisional application No. 61/821,761, filed on May 10, 2013.

(51) Int. Cl.
*G06K 9/00* (2006.01)
*G06T 11/00* (2006.01)
*A61B 6/03* (2006.01)
*A61B 6/00* (2006.01)

(52) U.S. Cl.
CPC .............. *G06T 11/005* (2013.01); *A61B 6/037* (2013.01); *A61B 6/5264* (2013.01); *G06T 11/006* (2013.01); *G06T 2211/412* (2013.01)

(58) Field of Classification Search
CPC .............. G06T 11/005; G06T 11/006; G06T 2211/412; A61B 6/037; A61B 6/5264
USPC .................................................. 382/128, 131
See application file for complete search history.

(56) References Cited

U.S. PATENT DOCUMENTS

| | | | | |
|---|---|---|---|---|
| 7,945,079 B2 * | 5/2011 | Rosen | ........................... | 382/128 |
| 2010/0290683 A1 * | 11/2010 | Demeester et al. | .......... | 382/131 |
| 2011/0268334 A1 * | 11/2011 | Ra et al. | ....................... | 382/131 |
| 2012/0078089 A1 * | 3/2012 | Wollenweber et al. | ...... | 600/427 |

* cited by examiner

*Primary Examiner* — Tom Y Lu
(74) *Attorney, Agent, or Firm* — Quarles & Brady LLP

(57) ABSTRACT

Systems and methods for compensating motion artifacts in positron emission tomography ("PET") imaging based on medical images acquired with a medical imaging system are provided. In some embodiments, the method includes acquiring PET data from a subject with a PET system during which at least a portion of the subject is undergoing motion, and providing medical images acquired from the subject using a medical imaging system, the medical images including regions depicting motion. The method also includes estimating, from the medical images, motion information associated with the motion of the at least a portion of the subject, and reconstructing a motion-corrected PET image using the PET data using a reconstruction algorithm that incorporates the motion information into a system matrix.

12 Claims, 4 Drawing Sheets

SYSTEMS AND METHODS FOR MOTION CORRECTION IN POSITRON EMISSION TOMOGRAPHY IMAGING

CROSS-REFERENCE TO RELATED APPLICATIONS

This application claims the benefit of U.S. Provisional Patent Application Ser. No. 61/821,761, filed on May 10, 2013, and entitled "Compensation for External and Internal Motion in PET-MR."

STATEMENT REGARDING FEDERALLY SPONSORED RESEARCH

This invention was made with government support under EB012326 awarded by the National Institutes of Health. The government has certain rights in the invention.

BACKGROUND OF THE INVENTION

The field of the invention is systems and methods for medical and molecular imaging. More particularly, the invention relates to systems and methods for motion correction in positron emission tomography ("PET") imaging.

Positrons are positively charged electrons that are emitted by radionuclides that have been prepared using a cyclotron or other device. These are employed as radioactive tracers called "radiopharmaceuticals" by incorporating them into substances, such as glucose or carbon dioxide. The radiopharmaceuticals are administered to a patient and become involved in biochemical or physiological processes such as blood flow, fatty acid and glucose metabolism; and protein synthesis.

Some common clinical applications of PET imaging include oncology and cardiology for detecting and staging of cancer and cardiac diseases, as well as for monitoring treatment response. In a PET imaging scan, a radioactive tracer that emits positrons is administered to the body of a patient. The released positrons immediately annihilate, creating photon pairs with 511 keV energies that propagate in opposite directions from the annihilation point. The volume distribution and concentration of radioactive tracers in the body is determined based on the detection of radiation outside the patient.

Generally, a PET scanner includes one or more rings of detectors that encircle the patient and convert the energy of each 511 keV photon into a flash of light that is sensed by a radiation detector, such as a photomultiplier tube ("PMT"). Coincidence detection circuits connected to the radiation detectors record only those photons that are detected simultaneously by two detectors located on opposite sides of the patient. The number of such simultaneous events indicates the number of positron annihilations that occurred along a virtual line joining the two opposing detectors, called the line of response ("LOR"). An image indicative of the tissue concentration of the positron emitting radionuclide is created by determining the number of such annihilation events at each location within the field-of-view.

Motion artifacts commonly found in PET images are mainly due to irregular motion, as well as periodic internal motion from respiratory and cardiac activity. In particular, subject motion is generally difficult to avoid, due to the long scan durations (up to several minutes) necessary for PET imaging to be of clinical value, leading to image degradation, or blurring, and severe artifacts when motion has large amplitudes. On the other hand, physiological activity causes organs, such as heart muscle, lung, or abdominal organs, to change location, shape, or local tissue density, resulting in complex, non-rigid movement patterns. These effects limit the spatial resolution that can be achieved in PET imaging much more than physical factors, such as detector size, photon non-collinearity and positron range of travel. For instance, the physical factors affecting spatial resolution generally contribute to a deterioration of spatial resolution on the order of 1-3 mm, as compared to 5-15 mm due to organ motion from respiratory activity. Clinical situations when motion may become important include, for example, small perfusion defects present in the myocardium and small liver, or lung tumors, which generally are not detectable, or are much less visible, on images including motion artifacts. Therefore, absent motion corrections may result in different diagnostic outcomes.

Many approaches have been explored in the effort to correct motion artifacts. Depending on whether the motion is estimated from the acquired PET data or by other instrumentation, the approaches can be divided into two groups: auto-correction and assisted-correction. For the auto-correction techniques, the measured PET data are divided into temporal frames, or gates, and the motion is then estimated between temporal frames from the PET data. The estimated motion field can then be used to transform the reconstructed images or the sinograms of each temporal frame to a reference frame. The accuracy of motion estimation using this approach is limited by the noise of PET images, which increases as the data set is divided into temporal frames for a dynamic image sequence. Moreover, the fact that the motion estimation relies on the generation of images or sinograms limits its temporal resolution. Thus, such methods are not suitable when the activity distribution is fast changing or the object is fast moving. For example, cardiac imaging of rapid dynamic functions, such as myocardial blood flow, may not be possible using a gated approach due to the substantial noise associated with rejecting a large number of detected events in low count frames. The reconstruction algorithms of the assisted-correction approaches are similar to auto-correction techniques except that the motion information is instead measured using an instrument other than the PET camera, such as video/infrared cameras, and approaches with structured light.

Therefore, given at least the above, there is a need for systems and methods that correct for internal and external motion artifacts commonly present in PET imaging.

SUMMARY OF THE INVENTION

The present invention overcomes the aforementioned drawbacks by providing systems and methods directed to compensation of motion artifacts in positron emission tomography ("PET") imaging. In particular, the present disclosure provides a robust and accurate methodology for correcting PET acquisitions by identifying external and internal motion patterns from medical images from a subject, such magnetic resonance ("MR") or computed tomography ("CT") images, and incorporating the determined motion into the PET image reconstruction process.

In one aspect of the present invention a method for compensating motion artifacts in positron emission tomography ("PET") imaging based on medical images acquired with a medical imaging system is provided. The method includes acquiring PET data from a subject with a PET system during which at least a portion of the subject is undergoing motion, and providing medical images acquired from the subject using a medical imaging system, the medical images including regions depicting motion. The method also includes estimating, from the medical images, motion information associated with the motion of the at least a portion of the subject, and reconstructing a motion-corrected PET image using the PET data and a reconstruction algorithm that incorporates the motion information into a system matrix.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

The present disclosure is directed to systems and methods for compensating motion artifacts present in positron emission tomography ("PET") imaging using motion pattern information determined from medical images, such as magnetic resonance ("MR") images or computed tomography ("CT") images, acquired from a subject while at least a portion of the subject is undergoing motion. As will be described, such motion information may be incorporated into the reconstruction process of PET data, which significantly improves the potential quality and quantitative accuracy of the reconstructed PET images. As such, the present disclosure provides a methodology for correcting cardiac, respiratory, and other motion artifacts that may otherwise interfere with the visibility, as well as the accuracy, of structures depicted in PET images.

The approach of the present disclosure allows for significantly improved PET spatial resolution by removing image blurring due to motion. In addition, image noise may be significantly reduced because all PET events generated during acquisition may be utilized to generate an image, as opposed to previous reconstruction methods that only use a fraction of events to provide an image consistent with a particular motion state. Artifacts in PET imaging due to motion mismatches between the emission and attenuation datasets may also be removed using methodologies described by the present disclosure. Furthermore, the inherent spatial non-uniformity of image properties may be reduced, including bias and resolution due to motion-based spatially variant regularizer present in the reconstruction algorithm.

Figure 1:
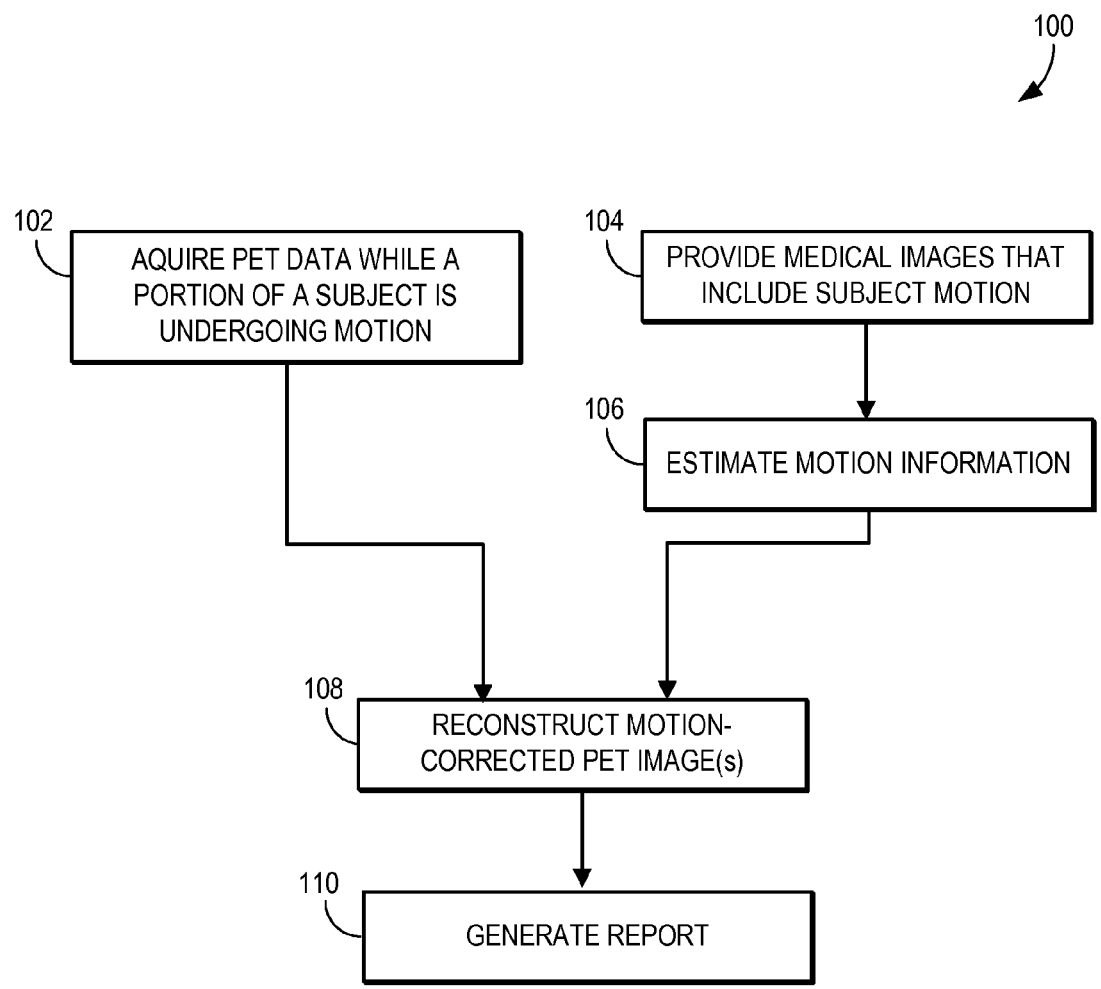
FIG. 1 is a flowchart setting forth the steps of a process for correcting PET image data in accordance with the present disclosure.

Referring specifically to FIG. 1, a process 100 for correcting PET image data in accordance with the present disclosure is shown. The process 100 may begin at process block 102 where PET data may be acquired from a subject using a PET system while at least a portion of a subject is undergoing motion. As described, such motion may include internal motion due to physiological activity, such as cardiac or respiration activity, or external, aperiodic motion. At process block 104 medical images acquired from the subject using a medical imaging system, such as a MR system or a CT system, may be provided for purposes including motion correction.

In some embodiments, the PET system and medical imaging system may be integrated into a combined imaging system, such as a PET-MR system, or a PET-CT system. As illustrated in FIG. 1, process blocks 102 and 104 may then occur substantially contemporaneously. That is, PET data may be acquired substantially contemporaneously with acquisition of the medical imaging data using a combined imaging system. For example, both the MR data and PET data receive a time stamp when they are acquired such that an MR signal acquired at substantially the same instance in time as a PET signal is employed to correct for motion at that moment in time. As such, simultaneous acquisition of PET and MRI allows to estimate continuously, for example, organ motion from MR imaging sequences or specialized MR pulse sequences. In other embodiments, the medical imaging system may be separate from the PET system, including a MR or a CT imaging system. Therefore, medical imaging data may be acquired sequentially, contemporaneously, or in an interleaved manner, with respect to PET data acquisition.

The acquired medical images may include motion effects, or motion artifacts, resulting from free breathing, or breath-held, pattern, cardiac activity, or other movement of the subject. In some aspects, the medical images may include MR images, acquired using any imaging sequences suitable for estimating motion fields. In other aspects, the medical images may include CT images, for example, acquired over a sufficiently long period of time so as to allow estimation of internal and external motion.

As one non-limiting example, the medical images acquired at step 104 can be acquired by directing an MRI system to perform MR tagging, whereby a spatially periodic magnetization pattern is induced in a subject using a combination of radio frequency pulses ("RF") and field gradient pulses. The evolution of the magnetization pattern, in dependence of motion factors, may then be monitored via the acquisition of subsequent MR images.

As another non-limiting example, the medical images acquired at step 104 can be acquired by directing an MRI system to perform a navigated pulse sequence, such as one that utilizes a steady-state free-precession ("SSFP") acquisition interleaved with the acquisition of pencil-beam navigator echo signals. In some configurations, navigator echo signals may be generated using two-dimensional RF excitation pulses that selectively excite circular regions along an image plane and uniformly along an axis perpendicular to the image plane. In this manner, a longitudinal cylinder of tissue through, say a diaphragm dome, can be acquired for use in tracking target locations, markers, or anatomical landmarks, such as a lung-liver interface. The position of such target locations can be extracted from the navigator profile using, for example, an edge detection algorithm. Other types of navigators could also be implemented to measure subject motion, including circular navigators and cloverleaf navigators. In addition, other specialized pulse sequences that provide direct measures of subject motion may also be utilized, including velocity-encoded pulse sequences.

Next, at process block 106, motion information may be estimated from the medical images provided at process block 104. In some embodiments, non-rigid motion may be derived from the medical images, in contrast to previous methods, which typically estimate only rigid body motion. As described, such medical images may be generated using MR imaging sequences intrinsically sensitive to motion. Specifically with respect to MR tagging, spatial modulation of magnetization resulting from application of an MR tagging sequence creates a periodic modulation of magnetization in space by exciting (and subsequently dephasing) an interference pattern in the transverse magnetization due to a pair of rectangular hard RF pulses separated in time by a gradient field pulse. This periodic magnetization pattern is distorted with movement of the imaged tissue, and therefore indicates positional changes occurring between the tagging preparation pulses and image acquisition that may be utilized to estimate motion.

In some embodiments, motion information may be estimated at process block 106 based on MR navigator data. For example, respiratory motion may be determined by way of tracking an anatomical location, such as a lung-liver interface, during the respiratory cycle. This motion can be tracked using navigator signals collected prior to each slice acquisition to monitor the respiratory phase of that slice. Internal motion information obtained in this manner allows accurate monitoring of the respiratory cycle and handling of respiratory cycle irregularities. To cover a maximum number of respiratory positions for each slice, each single-slice steady-state free-precession acquisition may be repeated a number of times. After a given slice has been acquired, a different slice may be acquired using the same procedure, until an entire volume of interest has been covered.

In order to estimate motion information at process block 106 a B-spline non-rigid image registration approach may be used, which includes similarity measures, such as the sum of the squared difference ("SSD") and mutual information ("MI"), and a constraint term for motion field regularization. Specifically, motion fields may be estimated by minimizing the following cost function:

$$\Phi = M(f_T, Tf_S) + \beta R(T) \qquad (1);$$

where $f_T$ and $f_S$ are the target and source image respectively; T is a motion, or time warp, operator; M is a similarity measure; R(T) is a regularizer; and β is a regularization parameter. Because motion estimation is generally an ill-posed inverse problem, regularization is used in Eqn. (1) to achieve a stable and realistic solution. Requiring the estimated motion to be invertible (i.e., the determinant of Jacobian of motion must be positive) has been shown to regularize the motion estimation problem. A simple regularizer that penalizes the difference of the adjacent B-spline coefficients can be used. The regularization parameter, β, can be increased until all Jacobian determinant values at all voxels are positive. This regularization parameter can be applied to both B-spline SSD and MI based motion estimation algorithms.

In some embodiments, cubic B-spline interpolation can be used for images and estimated motion fields. For motion fields, B-spline knots (coefficients) can be located with a spacing of, say, 4 pixels in each x, y, z direction. Local minima problem can be avoided using a bi-level multiresolution scheme. In particular, motion fields may be estimated between adjacent phases and B-spline interpolation may be used for the composition of motion fields to estimate motions between different phases other than adjacent phases.

As one example, noting f (t,x) as a medical image volume at a given respiratory phase, t, motion information can be estimated using a registration algorithm that searches for an optimal three-dimensional cubic B-splice motion field $\hat{g}(t \to t', x)$ between a pair of volumes f (t,x) and f (t',x), such that, $$\hat{g}(t \to t', x) = \qquad (2)$$

$$\underset{g}{\mathrm{argmin}} \left\{ \frac{1}{N} \sum_x (f(t, g(t \to t', x)) - f(t', x))^2 + \beta R(g(t \to t', x)) \right\};$$

where x is the voxel position, N is the total number of voxels in one image volume, β is the regularization parameter, and R(•) is the regularizer. The regularization term penalizes the differences between adjacent B-spline coefficients and imposes local invertibility. As mentioned above, a bi-level multiresolution strategy can be used to increase the robustness and speed of the registration algorithm.

Once the motion information is estimated at process block 106, the motion information may be used to simultaneously reconstruct a PET image while compensating for the effects of the subject motion, as indicated at step 108. In particular, this result can be achieved by incorporating the motion information directly into the system matrix utilized in the PET reconstruction algorithm. In particular, this result can be achieved by incorporating the motion information directly into the system matrix utilized in the PET reconstruction algorithm. As one example, the motion-dependent system matrix can have the following form:

$$P_t = NBA_tGM_t \qquad (3);$$

where $M_t$ is a nonrigid warping operator that registers a given phase t to a reference phase, and which is based on the estimated motion information; G is the forward-projection operator; $A_t$ is a diagonal matrix containing the LOR attenuation correction factors for each frame, t; B models the point spread function ("PSF") blurring effects in the projection space; and N is the diagonal matrix of detector normalization factors.

Incorporating the motion information into the system matrix utilized in the PET image reconstruction significantly improves the spatial resolution, contrast recovery, and quantitation achieved in the PET image without compromising the statistics in the image, as is the case in gated PET approaches. It is noted that, as mentioned above, the motion information can be estimated from medical images acquired at a different time from the PET data, although preferably when the corresponding motion phase of the PET events can be matched with the motion phase of the MR-derived motion. Such matching can be performed using various modalities and techniques, including electrocardiogram ("ECG") measures, as well as measurements using reflective trackers, MR navigators and so forth.

In some embodiments, the PET image reconstruction can be performed using an ordered-subset expectation maximization ("OSEM") algorithm. For instance, the following updating loop can be used based on the system matrix of Eqn. (3):

$$f^{iter+1} = \qquad (4)$$

-continued $$\frac{f^{iter}}{\sum_t D_t M_t^T G^T A_t BN1_t} \sum_t M_t^T G^T B \left\{ \frac{y_t}{BGM_t f^{iter} + (A_t N)^{-1}(\bar{s}_c + \bar{r})} \right\};$$

where $D_t$ is the relative duration of frame t; $y_t$ is a sinogram of size I, which is the number of sinogram bins, containing the events rebinned into M motion frames; f is a vector of size J, which is the number of voxels, containing the voxels' radiotracer concentration; $\bar{s}_c$ and $\tilde{r}$ contains estimated scattered and random coincidences, respectively, that contribute to the expected data in each motion frame; and $1_t$ is a column vector of size I with all ones.

PSF modeling incorporation into the system matrix can be performed to reduce partial volume effects that are caused by the limited PET spatial resolution, and which can lead to underestimation of reconstructed uptake values. Partial volume effects can be significantly reduced by modeling the PSF of the scanner in either projection or image space, and by incorporating that information into the system matrix utilized in the image reconstruction, as mentioned above.

As one example, PSF modeling can be performed in the image domain, where it is straightforward to implement in a list-mode reconstruction. To assess the resolution throughout the FOV and to compute the operator, B, in Eqn. (3), point source measurements in air can be used. For instance, 0.5 mm F-18 point source measurements in air can be used.

As one non-limiting example, a for given axial position, four point sources can be simultaneously positioned at different radial positions, each with different azimuthal angles across the scanner FOV. Coincidences for two or more different axial positions can then be measured. The point-source data can then be reconstructed, and the reconstructed point-source profiles fitted with Gaussian functions to extract the width parameters (a) along radial, tangent, and axial directions. These values can then be used to obtain a for any given point within the FOV by linear interpolation. This PSF information can then be incorporated into the system matrix, as described above.

Although an OSEM reconstruction algorithm is described above, it will be appreciated by those skilled in the art that the motion, attenuation, and PSF information can also be incorporated into the system matrix used for any other suitable image reconstruction algorithm, including an iterative maximum likelihood expectation maximization ("MLEM") reconstruction or a maximum a posteriori ("MAP") reconstruction algorithm. With a MAP reconstruction, the motion information can also be incorporated into the spatial priors to yield an accurate reconstruction of the PET activity distribution while modeling organ motion in the projector of the reconstruction algorithm.

In addition, motion information estimated at process block 106 may be used to generate motion-dependent attenuation maps to correct for spatial mismatches between emission and attenuation data. This is an important step because mismatches between the emission and attenuation datasets due to motion have been shown to create artifacts in the final PET image. Such artifacts may impair the accuracy of the diagnostic, and currently no techniques for correcting them in a robust and accurate way other than as described herein.

The above-described reconstruction algorithm could be applied to any PET-MRI scanner where the PET data is acquired simultaneously or sequentially to the MRI data. It could also be applied to any PET-CT scanner where the CT data is acquired over a sufficiently long period of time to allow estimation of the internal and external motion. The motion-corrected PET image(s) generated at process block 108 not only have the best spatial resolution achievable, on account of correction due to motion, but also the lowest noise level possible since all the PET events from an acquisition step may be formulated into a single image, in contrast to previous techniques that include separating the PET acquisition into consecutive images containing a fraction of all PET events. In addition, motion corrected PET image(s) generated at process block 108 also have the desirable uniformity of image properties for task-based applications, such as lesion detection and quantification since the image quality is normalized by the degree of motion at each voxel. In this manner motion correction may be provided for both internal organs as well as external motion. Finally, at process block 110 a report may be generated, which may include the reconstructed PET images in addition to any other suitable information, including information about the estimated motion.

Figure 2:
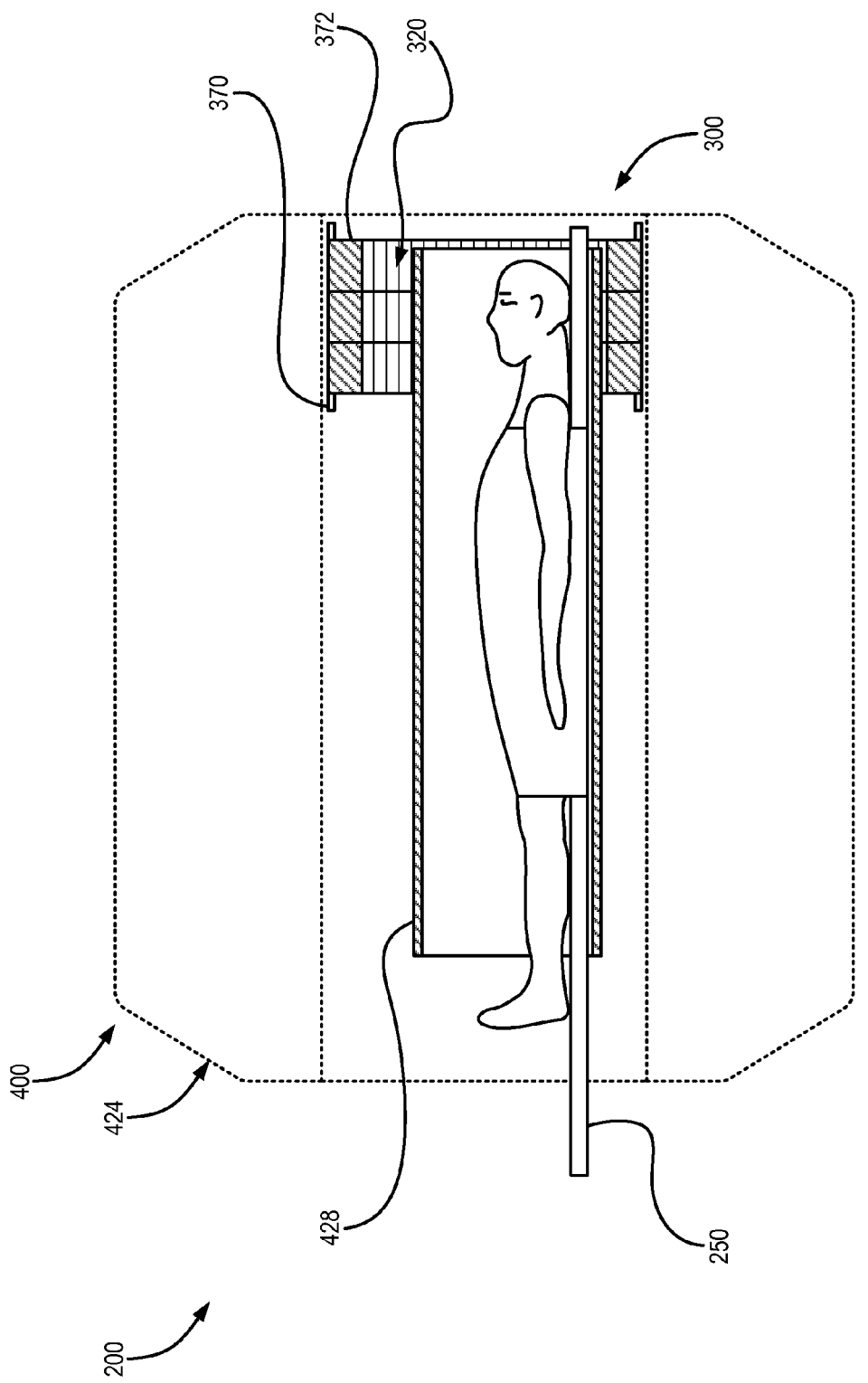
FIG. 2 is a pictorial view of a cross-section of a combination positron emission tomography (PET) imaging system and magnetic resonance imaging (MRI) system which employs the present invention.

Referring now to FIG. 2, the present disclosure may be implemented using a combined or simultaneous MR-PET system 200. The system 200 can be conceptualized as including an MRI system 400 having a cylindrical magnet assembly 424 which receives a subject to be imaged. Disposed within the magnet assembly 424 is a PET system 300 that includes plurality of PET detector rings 372 supported by a cylindrical PET gantry 370. Accordingly, each detector ring 372 has an outer diameter dimensioned to be received within the geometry of the MRI system 400. In other configurations, a single PET detector ring may be utilized. A patient table 250 is provided to receive a patient to be imaged. The gantry 370 is slidably mounted on the patient table 250 such that its position can be adjusted within the magnet assembly 424 by sliding it along the patient table 250. An RF coil 428 is employed to acquire MR signal data from a patient and is positioned between the PET detector rings 272 and the patient to be imaged. PET and MR data acquisitions are carried out on the patient, either simultaneously, in an interlaced or interleaved manner, or sequentially. Combined PET/MR imaging systems have been described, for example, in U.S. Pat. No. 7,218,112 and in U.S. Patent Application No. 2007/0102641, which are incorporated herein by reference.

Figure 3:
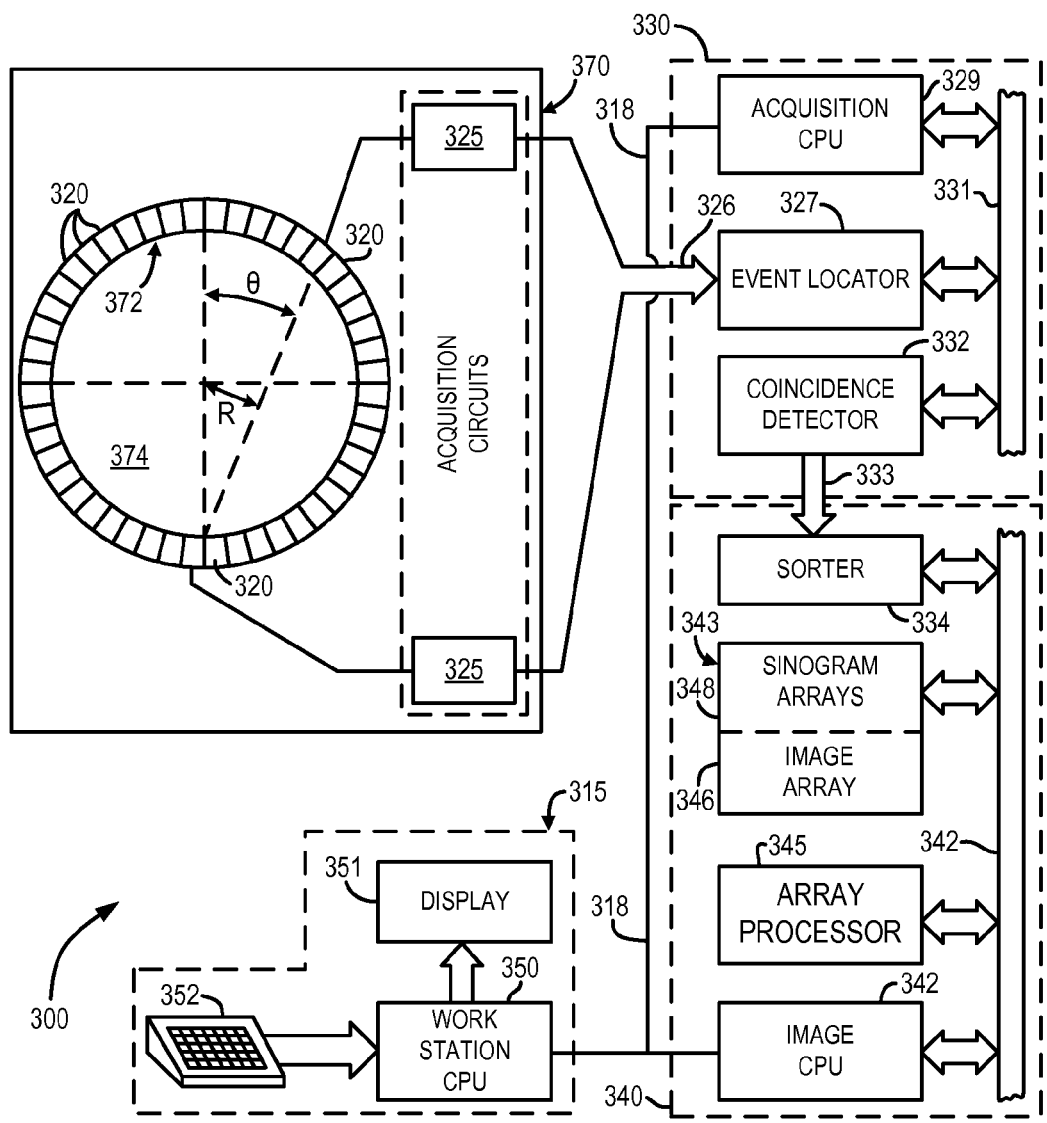
FIG. 3 is a schematic diagram of the PET imaging system portion of the system of FIG. 2.

Referring particularly to FIG. 3, the PET system 300 includes the gantry 370, which supports the detector ring assembly 372. The detector ring 372 includes detector units 320. The signals produced by the detector units 320 are then received by a set of acquisition circuits 325, which produce digital signals indicating the line of response and the total energy. These signals are sent through a communications link 326 to an event locator circuit 327. Each acquisition circuit 325 also produces an event detection pulse ("EDP") which indicates the exact moment the scintillation event took place.

The event locator circuits 327 form part of a data acquisition processor 330, which periodically samples the signals produced by the acquisition circuits 325. The processor 330 has an acquisition CPU 329 which controls communications on local area network 318 and a backplane bus 331. The event locator circuits 327 assemble the information regarding each valid event into a set of digital numbers that indicate precisely when the event took place and the position of the scintillator crystal which detected the event. This event data packet is conveyed to a coincidence detector 332 which is also part of the data acquisition processor 330.

The coincidence detector 332 accepts the event data packets from the event locators 327 and determines if any two of them are in coincidence. Coincidence is determined by a number of factors. First, the time markers in each event data packet must be within a preset time of each other, and second, the locations indicated by the two event data packets must lie on a straight line. Events that cannot be paired are discarded, but coincident event pairs are located and recorded as a coincidence data packet. As will be described, the coincidence data packets can be corrected for motion of the subject during the acquisition using information received from the MRI system 400 of FIG. 4. Using this corrective information and the information in each coincidence data packet, a corresponding set of corrected coincidence data packets can be calculated. As will be described, each coincidence data packet can, thus, be corrected to change its projection ray, (R, θ) by an amount corresponding to the movement of the subject, as determined using information from the MRI system 400 of FIG. 4.

The corrected coincidence data packets are conveyed through a link 333 to a sorter 334 where they are used to form a sinogram. This corrective process is repeated each time corrective values are received from the MRI system. The correction is made on those coincidence data packets that have accumulated since the receipt of the previous corrective values.

The sorter 334 forms part of an image reconstruction processor 340. The sorter 334 counts all events occurring along each projection ray (R, θ) and organizes them into a two dimensional sinogram array 348 which is stored in a memory module 343. In other words, a count at sinogram location (R, θ) is increased each time a corrected coincidence data packet at that projection ray is received. Due to the corrections made to the coincidence events, the sinogram that is formed during the scan depicts the subject being examined in the reference position despite subject motion that occurs during the scan. The image reconstruction processor 340 also includes an image CPU 342 that controls a backplane bus 341 and links it to the local area network 318. An array processor 345 also connects to the backplane 341 and it reconstructs an image from the sinogram array 348. The resulting image array 346 is stored in memory module 343 and is output by the image CPU 342 to the operator work station 315.

The operator work station 315 includes a CPU 350, a display 351 and a keyboard 352. The CPU 350 connects to the network 218 and it scans the keyboard 252 for input information. Through the keyboard 352 and associated control panel switches, the operator can control the calibration of the PET scanner and its configuration. Similarly, the operator can control the display of the resulting image on the display 351 and perform image enhancement functions using programs executed by the work station CPU 350.

Figure 4:
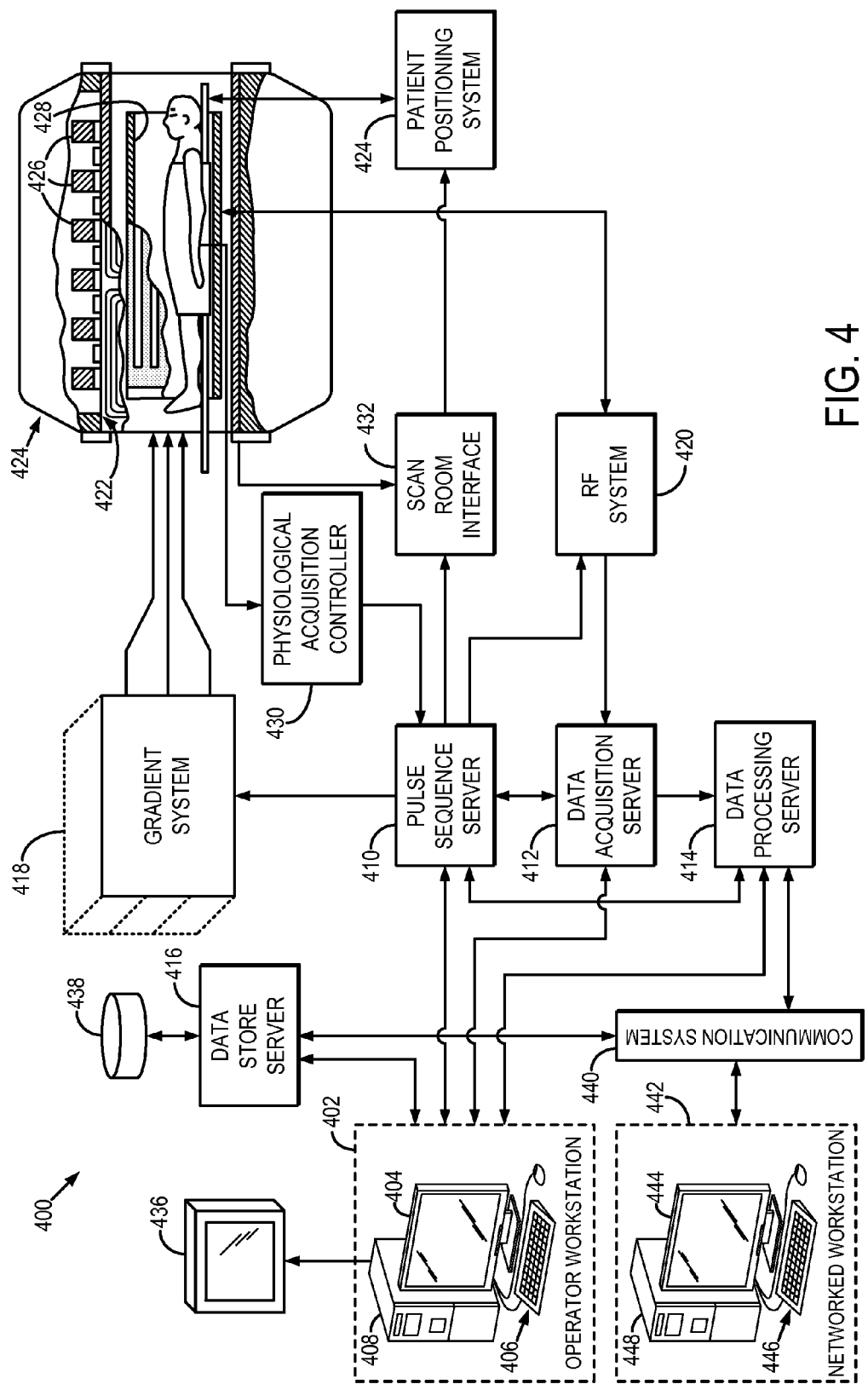
FIG. 4 is a schematic diagram of the MRI system portion of the system of FIG. 2.

Referring to FIG. 4, the MRI system 400 is illustrated in further detail. The MRI system 400 includes an operator workstation 402, which will typically include a display 404; one or more input devices 406, such as a keyboard and mouse; and a processor 408. The processor 408 may include a commercially available programmable machine running a commercially available operating system. The operator workstation 402 provides the operator interface that enables scan prescriptions to be entered into the MRI system 400. In general, the operator workstation 402 may be coupled to four servers: a pulse sequence server 410; a data acquisition server 412; a data processing server 414; and a data store server 416. The operator workstation 402 and each server 410, 412, 414, and 416 are connected to communicate with each other. For example, the servers 410, 412, 414, and 416 may be connected via a communication system 440, which may include any suitable network connection, whether wired, wireless, or a combination of both. As an example, the communication system 440 may include both proprietary or dedicated networks, as well as open networks, such as the internet.

The pulse sequence server 410 functions in response to instructions downloaded from the operator workstation 402 to operate a gradient system 418 and a radiofrequency (RF) system 420. Gradient waveforms necessary to perform the prescribed scan are produced and applied to the gradient system 418, which excites gradient coils in an assembly 422 to produce the magnetic field gradients $G_x$, $G_y$, and $G_z$ used for position encoding magnetic resonance signals. The gradient coil assembly 422 forms part of a magnet assembly 424 that includes a polarizing magnet 426 and optionally a whole-body RF coil 428.

RF waveforms are applied by the RF system 420 to the RF coil 428, in order to perform the prescribed magnetic resonance pulse sequence. Responsive magnetic resonance signals detected by the RF coil 428 are received by the RF system 420, where they are amplified, demodulated, filtered, and digitized under direction of commands produced by the pulse sequence server 410. The RF system 420 includes an RF transmitter for producing a wide variety of RF pulses used in MRI pulse sequences. The RF transmitter is responsive to the scan prescription and direction from the pulse sequence server 410 to produce RF pulses of the desired frequency, phase, and pulse amplitude waveform. The generated RF pulses may be applied to the whole-body RF coil 428 or to one or more local coils or coil array.

The RF system 420 also includes one or more RF receiver channels. Each RF receiver channel includes an RF preamplifier that amplifies the magnetic resonance signal received by the coil 428 or by the local coil or coil array to which it is connected, and a detector that detects and digitizes the I and Q quadrature components of the received magnetic resonance signal. The magnitude of the received magnetic resonance signal may, therefore, be determined at any sampled point by the square root of the sum of the squares of the I and Q components $M=\sqrt{I^2+Q^2}$ and the phase of the received magnetic resonance signal may also be determined according to the following relationship $$\varphi = \tan^{-1}\left(\frac{Q}{I}\right).$$

The pulse sequence server 410 also optionally receives patient data from a physiological acquisition controller 430. By way of example, the physiological acquisition controller 430 may receive signals from a number of different sensors connected to the patient, such as electrocardiograph (ECG) signals from electrodes, or respiratory signals from a respiratory bellows or other respiratory monitoring device. Such signals are typically used by the pulse sequence server 410 to synchronize, or "gate," the performance of the scan with the subject's heart beat or respiration.

The pulse sequence server 410 also connects to a scan room interface circuit 432 that receives signals from various sensors associated with the condition of the patient and the magnet system. It is also through the scan room interface circuit 432 that a patient positioning system 434 receives commands to move the patient to desired positions during the scan.

The digitized magnetic resonance signal samples produced by the RF system 420 are received by the data acquisition server 412. The data acquisition server 412 operates in response to instructions downloaded from the operator workstation 402 to receive the real-time magnetic resonance data and provide buffer storage, such that no data is lost by data overrun. In some scans, the data acquisition server 412 does little more than pass the acquired magnetic resonance data to the data processor server 414. However, in scans that require information derived from acquired magnetic resonance data to control the further performance of the scan, the data acquisition server 412 is programmed to produce such information and convey it to the pulse sequence server 410. For example, during prescans, magnetic resonance data is acquired and used to calibrate the pulse sequence performed by the pulse sequence server 410. As another example, navigator signals may be acquired and used to adjust the operating parameters of the RF system 420 or the gradient system 418, or to control the view order in which k-space is sampled. In still another example, the data acquisition server 412 may also be employed to process magnetic resonance signals used to determine patient motion, and communicate such to the PET system 300 described with respect to FIG. 3 to perform motion correction or compensation. By way of example, the data acquisition server 412 acquires magnetic resonance data and processes it in real-time to produce information that is used to control the overall operation of the MR and PET imaging acquisitions.

The data processing server 414 receives magnetic resonance data from the data acquisition server 412 and processes it in accordance with instructions downloaded from the operator workstation 402. Such processing may, for example, include one or more of the following: reconstructing two-dimensional or three-dimensional images by performing a Fourier transformation of raw k-space data; performing other image reconstruction algorithms, such as iterative or backprojection reconstruction algorithms; applying filters to raw k-space data or to reconstructed images; generating functional magnetic resonance images; calculating motion or flow images; and so on.

Images reconstructed by the data processing server 414 are conveyed back to the operator workstation 402 where they are stored. Real-time images are stored in a data base memory cache (not shown in FIG. 4), from which they may be output to operator display 412 or a display 436 that is located near the magnet assembly 424 for use by attending physicians. Batch mode images or selected real time images are stored in a host database on disc storage 438. When such images have been reconstructed and transferred to storage, the data processing server 414 notifies the data store server 416 on the operator workstation 402. The operator workstation 402 may be used by an operator to archive the images, produce films, or send the images via a network to other facilities.

The MRI system 400 may also include one or more networked workstations 442. By way of example, a networked workstation 442 may include a display 444; one or more input devices 446, such as a keyboard and mouse; and a processor 448. The networked workstation 442 may be located within the same facility as the operator workstation 402, or in a different facility, such as a different healthcare institution or clinic.

The networked workstation 442, whether within the same facility or in a different facility as the operator workstation 402, may gain remote access to the data processing server 414 or data store server 416 via the communication system 440. Accordingly, multiple networked workstations 442 may have access to the data processing server 414 and the data store server 416. In this manner, magnetic resonance data, reconstructed images, or other data may exchanged between the data processing server 414 or the data store server 416 and the networked workstations 442, such that the data or images may be remotely processed by a networked workstation 442. This data may be exchanged in any suitable format, such as in accordance with the transmission control protocol (TCP), the internet protocol (IP), or other known or suitable protocols.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for compensating motion artifacts in positron emission tomography ("PET") imaging based on medical images acquired with a medical imaging system, the method comprising:
   a) acquiring PET data from a subject with a PET system during which motion of at least a portion of the subject is occurring;
   b) providing medical images acquired from the subject using a medical imaging system, the medical images including regions depicting motion;
   c) estimating, from the medical images, motion information indicative of the motion of the at least a portion of the subject that occurred in step a); and
   d) simultaneously reconstructing a PET image from the PET data while compensating for effects of the motion that occurred in step a) using an iterative reconstruction algorithm that incorporates the estimated motion information into a system matrix, whereby motion correction is enforced at each iteration of the image reconstruction algorithm by the system matrix.

2. The method of claim 1, wherein the motion includes at least one of a cardiac motion, a respiratory motion, and a non-periodic motion.

3. The method of claim 1, wherein step b) includes acquiring the medical images using at least one of a magnetic resonance imaging (MRI) system and a computed tomography (CT) system.

4. The method of claim 3, wherein the medical imaging system and the PET system form an integrated system.

5. The method of claim 1, wherein estimating the motion information at step (c) includes minimizing a cost function defined as:

$$\Phi = M(f_T, Tf_S) + \beta R(T)$$

wherein $f_T$ and $f_s$ are a target and a source image, respectively, T is a motion operator, M is a similarity measure, R(T) is a regularizer and $\beta$ is a regularization parameter.

6. The method of claim 5, wherein the similarity measure includes one of a sum of squared difference and a mutual information parameter.

7. The method of claim 1, wherein the reconstruction algorithm includes an ordered-subset expectation maximization ("OSEM") reconstruction.

8. The method of claim 1, wherein the reconstruction algorithm includes an iterative maximum likelihood expectation maximization ("MLEM") reconstruction.

9. The method of claim 1, wherein the reconstruction algorithm includes a maximum a posteriori ("MAP") reconstruction algorithm with the motion information further incorporated into spatial priors.

10. The method of claim 1, further comprising providing a model of a point-spread function (PSF) for the PET system and wherein step d) includes incorporating the model of the PSF into the system matrix of the reconstruction algorithm.

11. The method of claim 1, wherein the medical images are magnetic resonance images acquired using a pulse sequence that tags motion.

12. The method of claim 1, wherein the medical images are magnetic resonance images acquired using a pulse sequence that also acquires navigator data, and the motion estimated in step c) is estimated from the navigator data.

* * * * *